US007449200B2

(12) United States Patent
Sung et al.

(10) Patent No.: US 7,449,200 B2
(45) Date of Patent: Nov. 11, 2008

(54) NANOPARTICLES FOR PROTEIN/PEPTIDE DELIVERY AND DELIVERY MEANS

(75) Inventors: Hsing-Wen Sung, HsinChu (TW); Mei-Chin Chen, Taipei County (TW); Po-Wei Lee, Jhonghe (TW); Hosheng Tu, Newport Beach, CA (US)

(73) Assignees: GP Medical, Inc., Newport Beach, CA (US); National Tsing Hua Univeristy, Hsinchu (TW)

( * ) Notice: Subject to any disclaimer, the term of this patent is extended or adjusted under 35 U.S.C. 154(b) by 219 days.

(21) Appl. No.: 11/405,066

(22) Filed: Apr. 17, 2006

(65) Prior Publication Data

US 2007/0243259 A1 Oct. 18, 2007

(51) Int. Cl.

| | |
|---|---|
| ***A61K 9/14*** | (2006.01) |
| ***A61K 38/28*** | (2006.01) |
| ***A61K 38/16*** | (2006.01) |
| ***A61K 38/00*** | (2006.01) |
| ***A61K 31/727*** | (2006.01) |
| ***A61M 31/00*** | (2006.01) |

(52) U.S. Cl. ............................... 424/489; 514/3; 514/8; 514/12; 514/56; 604/500

(58) Field of Classification Search ....................... None
See application file for complete search history.

(56) References Cited

U.S. PATENT DOCUMENTS

| | | | |
|---|---|---|---|
| 6,194,389 | B1 | 2/2001 | Johnston et al. |
| 6,475,995 | B1 | 11/2002 | Roy et al. |

OTHER PUBLICATIONS

Lin YH et al., "Preparation of nanoparticles composed of chitosan/poly-r-glutamic acid and evaluation of their permeability through Caco-2 cells" Biomacromolecules 2005;6:1104.

*Primary Examiner*—Cecilia J Tsang
*Assistant Examiner*—Marcela M Cordero Garcia

(57) ABSTRACT

The invention discloses the biodegradable nanoparticle for use in nanoparticle projectile bombardment as a carrier for administering proteins or peptides to an animal subject. The nanoparticles are composed of positively charged shell substrate, negatively charged core substrate with encapsulated bioactive agents of proteins or peptides.

10 Claims, 9 Drawing Sheets

(A) (B)

NANOPARTICLES FOR PROTEIN/PEPTIDE DELIVERY AND DELIVERY MEANS

FIELD OF THE INVENTION

The present invention is related to medical uses of nanoparticles comprising bioactive agents and their targeted epidermal delivery means via nanoparticle projectile bombardment.

BACKGROUND OF THE INVENTION

Production of pharmaceutically active peptides and proteins in large quantities has become feasible (Biomacromolecules 2004;5:1917-1925). The oral route is considered the most convenient way of drug administrations for patients. Nevertheless, the intestinal epithelium is a major barrier to the absorption of hydrophilic drugs such as peptides and proteins (J. Control. Release 1996;39:131-138). This is because hydrophilic drugs cannot easily diffuse across the cells through the lipid-bilayer cell membranes. Further more, following the oral drug delivery route, protein drugs are readily degraded by the low pH of gastric medium in the stomach.

Polymeric nanoparticles have been widely investigated as carriers for drug delivery (Biomaterials 2002;23:3193-3201). Much attention has been given to the nanoparticles made of synthetic biodegradable polymers such as poly-ε-caprolactone and polylactide due to their good biocompatibility (J. Drug Delivery 2000;7:215-232; Eur. J. Pharm. Biopharm. 1995;41:19-25). However, these nanoparticles are not ideal carriers for hydrophilic drugs because of their hydrophobic property. Some aspects of the invention relate to a novel nanoparticle system, composed of hydrophilic chitosan and poly(glutamic acid) hydrogels that is prepared by a simple ionic-gelation method. This technique is promising as the nanoparticles are prepared under mild conditions without using harmful solvents. It is known that organic solvents may cause degradation of peptide or protein drugs that are unstable and sensitive to their environments (J. Control. Release 2001; 73:279-291).

Chitosan (CS), a cationic polysaccharide, is generally derived from chitin by alkaline deacetylation (J. Control. Release 2004;96:285-300). It was reported from literature that CS is non-toxic and soft-tissue compatible (Biomacromolecules 2004;5:1917-1925; Biomacromolecules 2004;5: 828-833). Most commercially available CSs have quite large molecular weight (MW) and need to be dissolved in an acetic acid solution at a pH value of approximately 4.0 or lower that is sometimes impractical. However, there are potential applications of CS in which a low MW would be essential. Given a low MW, the polycationic characteristic of CS can be used together with a good solubility at a pH value close to physiological ranges (Eur. J. Pharm. Biopharm. 2004;57:101-105). Loading of peptide or protein drugs at physiological pH ranges would preserve their bioactivity. On this basis, a low-MW CS, obtained by depolymerizing a commercially available CS using cellulase, is disclosed herein in preparing nanoparticles of the present invention.

The γ-PGA, an anionic peptide, is a natural compound produced as capsular substance or as slime by members of the genus *Bacillus* (Crit. Rev. Biotechnol. 2001;21:219-232). γ-PGA is unique in that it is composed of naturally occurring L-glutamic acid linked together through amide bonds. It was reported from literature that this naturally occurring γ-PGA is a water-soluble, biodegradable, and non-toxic polymer. A related, but structurally different polymer, [poly(α-glutamic acid), α-PGA] has been used for drug delivery (Adv. Drug Deliver. Rev. 2002;54:695-713; Cancer Res. 1998;58:2404-2409). α-PGA is usually synthesized from poly(γ-benzyl-L-glutamate) by removing the benzyl protecting group with the use of hydrogen bromide. Hashida et al. used α-PGA as a polymeric backbone and galactose moiety as a ligand to target hepatocytes (J. Control. Release 1999;62:253-262). Their in vivo results indicated that the galactosylated α-PGA had a remarkable targeting ability to hepatocytes and degradation of α-PGA was observed in the liver.

U.S. Pat. No. 6,194,389 issued on Feb. 27, 2001, entire contents of which are incorporated herein by reference, discloses a method of administering a protein or peptide in a vertebrate subject by in situ microprojectile bombardment, comprising the steps of providing microprojectiles, the microprojectiles carrying polynucleic acid sequences; and accelerating the microprojectiles at the cells, with the microprojectiles contacting the cells at a speed sufficient to penetrate the cells and deposit the polynucleic acid sequences therein.

Skin is an attractive target for delivery of genetic therapies and vaccines. DNA transfer, usually delivered by gold particles, to epidermis by a gene gun was shown to be able to elicit humoral and cytotoxic lymphocyte responses due to the Langerhan's cells present in epidermis. However, the DNA coated on gold particles is liable to be digested by DNase and lacks the ability of controlled release. In view of the foregoing, an object of this invention is to provide new uses of nanoparticles encapsulated with plasmid DNA (PDNA) as a potential approach to genetic immunization by nanoparticle projectile bombardment.

SUMMARY OF THE INVENTION

Some aspects of the invention provide a novel nanoparticle system for topical transcutaneous delivery or targeted epidermal delivery of the biodegradable nanoparticles that encapsulate at least one bioactive agent of proteins or peptides via nanoparticle projectile bombardment. One aspect of the invention provides a method of preparing the nanoparticles using a simple and mild ionic-gelation method upon addition of bioactive agent containing polyanionic solution into chitosan solution. A particular aspect of the invention provides a method of preparing the nanoparticles by adding a mixture of poly-γ-glutamic acid (γ-PGA) and bioactive agent solution into a low molecular weight chitosan (low-MW CS) solution. In one embodiment, the molecular weight of a low-MW CS of the present invention is about 80 kDa or less, preferably at about 40 kDa, adapted for adequate solubility at a pH that maintains the bioactivity of protein and peptide drugs. It is stipulated that a chitosan particle with about 30-50 kDa molecular weight is kidney inert. In one embodiment, the chitosan raw material is a low molecular weight CS that is readily dissolvable in a solution with a pH range of about 5.0 to 6.5, preferably about 6.0 to 6.2.

In one embodiment, the chitosan dominates on surface of the nanoparticles as shell substrate and the negatively charged γ-PGA as core substrate. In another embodiment, a substantial portion of the surface of the nanoparticles is characterized with a positive surface charge. In a further embodiment, the nanoparticles of the present invention comprise at least one positively charged shell substrate and at least one negatively charged core substrate, wherein the core substrate is selected from a group consisting of heparin, heparin analogs, low molecular weight heparin, glycosaminoglycans, and alginate. In one embodiment, at least one bioactive agent or protein/peptide is conjugated with the negatively charged core substrate.

Some aspects of the invention provide a method of using nanoparticle projectile bombardment as a means for administering proteins or peptides encapsulated in non-metallic nanoparticles to an animal. In one embodiment, the non-metallic nanoparticles are biodegradable. In one preferred embodiment, the biodegradable nanoparticles provide sustained release of encapsulated proteins or peptides. In another embodiment, the nanoparticles are crosslinked with a crosslinking agent or with light, such as ultraviolet irradiation. In one embodiment, the degree of crosslinking is less than 50%. In another embodiment, the degree of crosslinking is in a range between 1% and 20% of the total available crosslink sites.

In a further embodiment, the nanoparticles of the present invention have a mean particle size between about 50 and 500 nanometers, preferably between about 100 and 300 nanometers, and most preferably between about 150 and 250 nanometers.

In some embodiments, the nanoparticles are loaded with a therapeutically effective amount of at least one bioactive agent, wherein the bioactive agent is selected from a group consisting of proteins, peptides, nucleosides, nucleotides, antiviral agents, antineoplastic agents, antibiotics, anti-inflammatory drugs, and combinations thereof. Further, the bioactive agent may be selected from a group consisting of calcitonin, cyclosporin, insulin, oxytocin, tyrosine, enkephalin, tyrotropin releasing hormone, follicle stimulating hormone, luteinizing hormone, vasopressin and vasopressin analogs, catalase, superoxide dismutase, interleukin-II, interferon, colony stimulating factor, tumor necrosis factor and melanocyte-stimulating hormone. In one preferred embodiment, the bioactive agent is an Alzheimer antagonist, calcitonin, vancomycin, chondroitin sulfate, hyaluronic acid, growth factor and protein drugs with pharmaceutically effective amount.

Some aspects of the invention provide nanoparticles characterized by enhancing intestinal or brain blood paracellular transport, each nanoparticle comprising a first component of at least one bioactive agent, a second component of low molecular weight chitosan, and a third component that is negatively charged, wherein the second component dominates on a surface of the. nanoparticle, wherein the at least one bioactive agent is an antagonist for Alzheimer's disease or is for treating Alzheimer's disease selected from the group consisting of memantine hydrochloride, donepezil hydrochloride, rivastigmine tartrate, galantamine hydrochloride, and tacrine hydrochloride. In a further embodiment, the at least one bioactive agent is insulin or insulin analog, wherein the molecular formula of the insulin is selected from a group consisting of $C_{254}H_{377}N_{65}O_{75}S_6$, $C_{257}H_{383}N_{65}O_{77}S_6$, $C_{256}H_{381}N_{65}O_{79}S_6$, $C_{267}H404N_{72}O_{78}S_6$, and the like.

Some aspects of the invention provide a method of administering a bioactive agent in an animal subject by in situ nano-projectile bombardment, comprising: selecting a target skin tissue of the animal subject, wherein the target skin tissue is selected from the group consisting of epidermis tissue, dermis tissue, and hypodermis tissue; providing nano-projectiles, wherein the bioactive agent is encapsulated in the nano-projectiles, each nano-projectile being in a nanoparticle form; and accelerating the nano-projectiles at the animal subject so that the nano-projectiles contact the animal's epidermis at a speed sufficient to penetrate the epidermis and lodge in the target skin tissue, wherein the accelerating step is carried out by a nano-projectile bombardment gun.

BRIEF DESCRIPTION OF THE DRAWINGS

Additional objects and features of the present invention will become more apparent and the disclosure itself will be best understood from the following Detailed Description of the Exemplary Embodiments, when read with reference to the accompanying drawings.

DETAILED DESCRIPTION OF THE EXEMPLARY EMBODIMENTS

Figure 1:
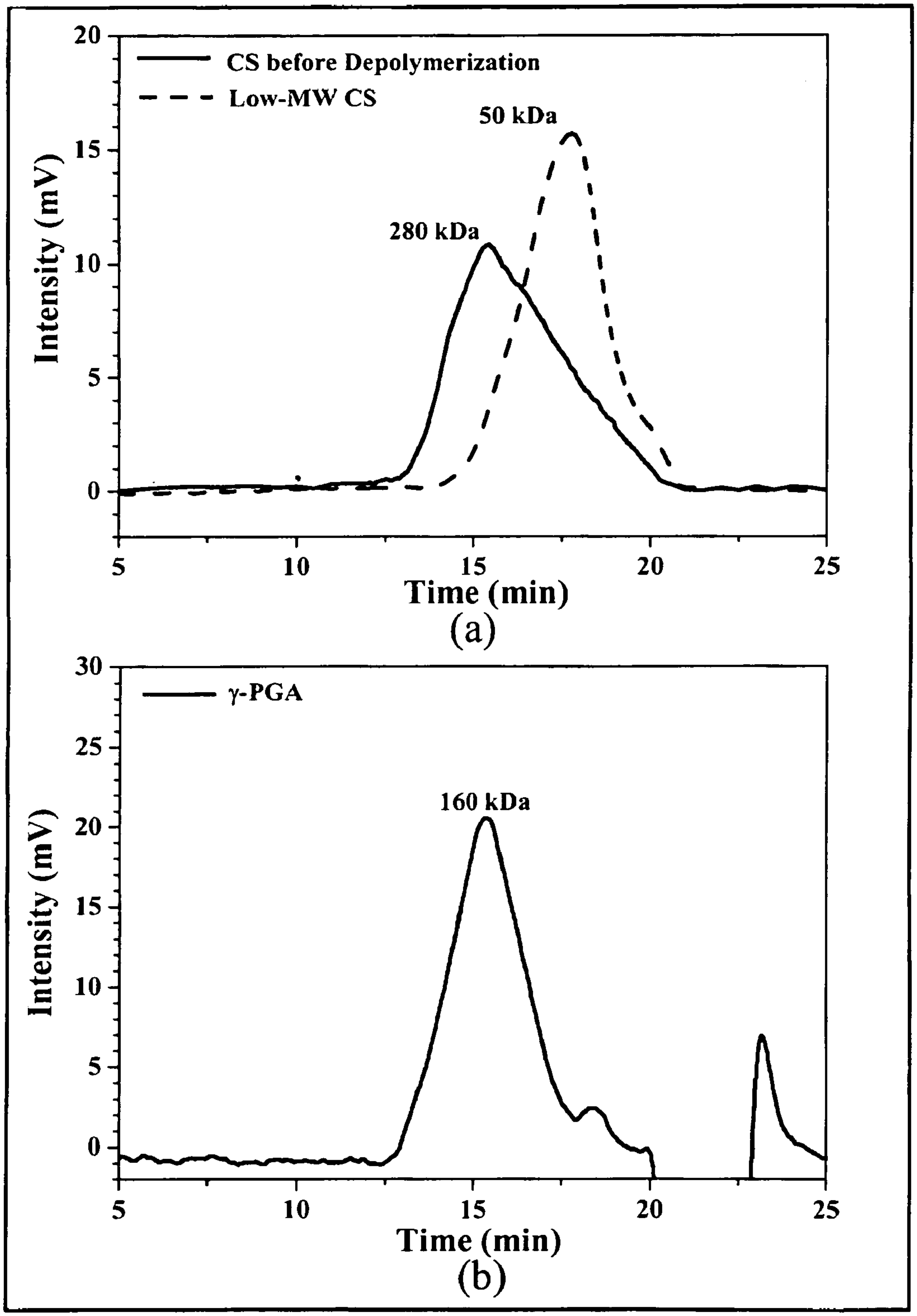
FIG. 1 shows GPC chromatograms of (a) standard-MW CS before depolymerization and the low-MW CS after depolymerization; (b) the purified γ-PGA obtained from microbial fermentation.

The preferred embodiments of the present invention described below relate particularly to preparation of nanoparticles composed of chitosan/poly-glutamic acid/insulin or chitosan/poly-glutamic acid/pDNA for transcutaneous delivery via nanoparticle projectile bombardment. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

γ-PGA is a naturally occurring anionic homo-polyamide that is made of L-glutamic acid units connected by amide linkages between α-amino and γ-carboxylic acid groups (Crit. Rev. Biotechnol. 2001;21:219-232). It is an exocellular polymer of certain *Bacillus* species that is produced within cells via the TCA cycle and is freely excreted into the fermentation broth. Its exact biological role is not fully understood, although it is likely that γ-PGA is linked to increasing the survival of producing strains when exposed to environmental stresses. Because of its water-solubility, biodegradability, edibility, and non-toxicity toward humans and the environment, several applications of γ-PGA in food, cosmetics, medicine, and water treatment have been investigated in the past few years.

EXAMPLE NO. 1

Materials and Methods of Nanoparticles Preparation

CS (MW ~$2.8\times10^5$) with a degree of deacetylation of approximately 85% was acquired from Challenge Bioproducts Co. (Taichung, Taiwan). Acetic acid, cellulase (1.92 units/mg), fluorescein isothiocyanate (FITC), phosphate buffered saline (PBS), periodic acid, sodium acetate, formaldehyde, bismuth subnitrate, and Hanks balanced salt solution (HBSS) were purchased from Sigma Chemical Co. (St. Louis, Mo.). Ethanol absolute anhydrous and potassium sodium tartrate were obtained from Merck (Darmstadt, Germany). Non-essential amino acid (NEAA) solution, fetal bovine serum (FBS), gentamicin and trypsin-EDTA were acquired from Gibco (Grand Island, N.Y.). Eagle's minimal essential medium (MEM) was purchased from Bio West (Nuaille, France). All other chemicals and reagents used were of analytical grade.

EXAMPLE NO. 2

Depolymerization of CS by Enzymatic Hydrolysis

Regular CS was treated with enzyme (cellulase) to produce low-MW CS according to a method described by Qin et al. with some modifications (Food Chem. 2004;84:107-115). A solution of CS (20 g/l) was prepared by dissolving CS in 2% acetic acid. Care was taken to ensure total solubility of CS. Then, the CS solution was introduced into a vessel and adjusted to the desired pH 5.0 with 2N aqueous NaOH. Subsequently, cellulase (0.1 g) was added into the CS solution (100 ml) and continuously stirred at 37° C. for 12 hours. Afterward, the depolymerized CS was precipitated with aqueous NaOH at pH 7.0-7.2 and the precipitated CS was washed three times with deionized water to remove cellulose and any very low molecular weight impurities. The resulting low-MW CS with a desired MW range was lyophilized in a freeze dryer (Eyela Co. Ltd, Tokyo, Japan).

The average molecular weight of the depolymerized CS was determined by a gel permeation chromatography (GPC) system equipped with a series of PL aquagel-OH columns (one Guard 8 μm, 50×7.5 mm and two MIXED 8 μm, 300×7.5 mm, PL Laboratories, UK) and a refractive index (RI) detector (RI2000-F, SFD, Torrance, Calif.). Polysaccharide standards (molecular weights range from 180 to 788,000, Polymer Laboratories, UK) were used to construct a calibration curve. The mobile phase contained 0.1M $NaH_2PO_4$ and 0.5M $NaNO_3$ and was brought to a pH of 2.0. The flow rate of mobile phase was 1.0 ml/min, and the columns and the RI detector cell were maintained at 30° C.

Factors limiting applications of most commercially available CSs are their high molecular weight and thus high viscosity and poor solubility at physiological pH ranges. Low-MW CS overcomes these limitations and hence finds much wider applications in diversified fields. It was suggested that low-MW CS be used as a parenteral drug carrier due to its lower antigen effect (Eur. J. Pharm. Biopharm. 2004;57:101-105). Low-MW CS was used as a non-viral gene delivery system and showed promising results (Int. J. Pharm. 1999; 178:231-243). Other studies based on animal testing showed the possibilities of low-MW CS for treatment of type 2 diabetes and gastric ulcer (Biol. Pharm. Bull. 2002;25:188-192). Several hydrolytic enzymes such as lysozyme, pectinase, cellulase, bromelain, hemicellulase, lipase, papain and the like can be used to depolymerize CS (Biochim. Biophys. Acta 1996;1291:5-15; Biochem. Eng. J. 2001;7:85-88; Carbohydr. Res. 1992;237:325-332). FIG. 1*a* shows GPC chromatograms of both standard-MW (also known as regular-MW) and low-MW CS. It is known that cellulase catalyzes the cleavage of the glycosidic linkage in CS (Food Chem. 2004; 84:107-115). The low-MW CS used in the study was obtained by precipitating the depolymerized CS solution with aqueous NaOH at pH 7.0-7.2. Thus obtained low-MW CS had a MW of about 50 kDa (FIG. 1*a*). In a preferred embodiment, the low molecular weight chitosan has a molecular weight of less than about 40 kDa, but above 10kDa. Other forms of chitosan may also be applicable, including chitin, chitosan oligosaccharides, and derivatives thereof.

It was observed that the obtained low-MW CS can be readily dissolved in an aqueous solution at pH 6.0, while that before depolymerization needs to be dissolved in an acetic acid solution with a pH value about 4.0. Additionally, it was found that with the low-MW CS, the prepared nanoparticles had a significantly smaller size with a narrower distribution than their counterparts prepared with the high-MW (also known as standard-MW) CS before depolymerization, due to its lower viscosity. As an example, upon adding a 0.10% γ-PGA aqueous solution into a 0.20% high-MW CS solution (viscosity 5.73±0.08 cp, measured by a viscometer), the mean particle size of the prepared nanoparticles was 878.3±28.4 nm with a polydispersity index of 1.0, whereas adding a 0.10% γ-PGA aqueous solution into the low-MW CS solution (viscosity 1.29±0.02 cp) formed nanoparticles with a mean particle size of 218.1±4.1nm with a polydispersity index of 0.3 (n=5).

EXAMPLE NO. 3

Production and Purification of γ-PGA

γ-PGA was produced by *Bacillus licheniformis* (ATCC 9945, Bioresources Collection and Research Center, Hsinchu, Taiwan) as per a method reported by Yoon et al. with slight modifications (Biotechnol. Lett. 2000;22:585-588). Highly mucoid colonies (ATCC 9945a) were selected from *Bacillus licheniformis* (ATCC 9945) cultured on the E medium (ingredients comprising L-glutaric acid, 20.0 g/l; citric acid, 12.0 g/l; glycerol, 80.0 g/l; $NH_4Cl$, 7.0 g/l; $K_2HPO_4$, 0.5 g/l; $MgSO_4.7H_2O$, 0.5 g/l; $FeCl_3.6H_2O$, 0.04 g/l; $CaCl_2.2H_2O$, 0.15 g/l; $MnSO_4.H_2O$, 0.104 g/l, pH 6.5) agar plates at 37° C. for several times. Subsequently, young mucoid colonies were transferred into 10 ml E medium and grown at 37° C. in a shaking incubator at 250 rpm for 24 hours. Afterward, 500 μl of culture broth was mixed with 50 ml E medium and was transferred into a 2.5-1 jar-fermentor (KMJ-2B, Mituwa Co., Osaka, Japan) containing 950 ml of E medium. Cells were cultured at 37° C. The pH was controlled at 6.5 by automatic feeding of 25% (v/v) $NH_4OH$ and/or 2M HCl. The dissolved oxygen concentration was initially controlled at 40% of air saturation by supplying air and by controlling the agitation speed up to 1000 rpm.

After 40 hours, cells were separated from the culture broth by centrifugation for 20 minutes at 12,000×g at 4° C. The supernatant containing γ-PGA was poured into 4 volumes of methanol and left overnight with gentle stirring. The resulting precipitate containing crude γ-PGA was collected by centrifugation for 40 minutes at 12,000×g at 4° C. and then was dissolved in deionized water to remove insoluble impurities by centrifugation for 20 minutes at 24,000×g at 4° C. The aqueous γ-PGA solution was desalted by dialysis (MWCO: 100,000, Spectrum Laboratories, Inc., Laguna Hills, Calif.) against distilled water for 12 hours with water exchanges several times, and finally was lyophilized to obtain pure γ-PGA.

The purified γ-PGA was verified by the proton nuclear magnetic resonance ($^1$H-NMR) and the FT-IR analyses.

Analysis of $^1$H-NMR was conducted on an NMR spectrometer (Varian Unityionva 500 NMR Spectrometer, Mo.) using DMSO-$d_6$ at 2.49 ppm as an internal reference. Test samples used for the FT-IR analysis first were dried and ground into a powder form. The powder then was mixed with KBr (1:100) and pressed into a disk. Analysis was performed on an FT-IR spectrometer (Perkin Elmer Spectrum RX1 FT-IR System, Buckinghamshire, England). The samples were scanned from 400-4000 $cm^{-1}$. The average molecular weight of the purified γ-PGA was determined by the same GPC system as described before. Polyethylene glycol (molecular weights of 106-22,000) and polyethylene oxide (molecular weights of 20,000-1,000,000, PL Laboratories) standards were used to construct a calibration curve. The mobile phase contained 0.1M $NaH_2PO_4$ and 0.2M $NaNO_3$ and was brought to a pH of 7.0.

Figure 2:
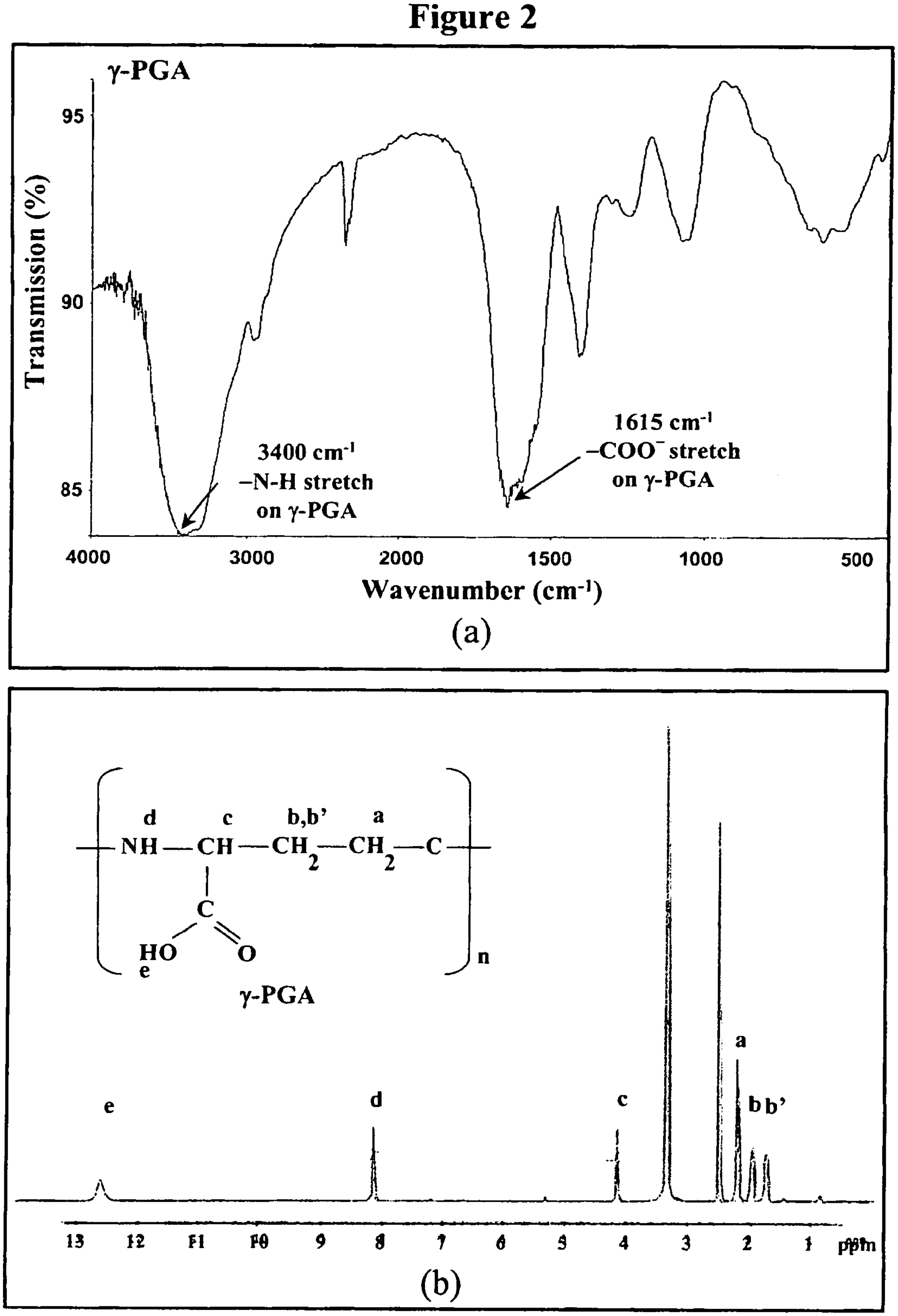
FIG. 2 shows. (a) FT-IR and (b) $^1$H-NMR spectra of the purified γ-PGA obtained from microbial fermentation.

The purified γ-PGA obtained from fermentation was analyzed by GPC, $^1$H-NMR, and FT-IR. As analyzed by GPC (FIG. 1*b*), the purified γ-PGA had a MW of about 160 kDa. In the FT-IR spectrum (FIG. 2*a*), a characteristic peak at 1615 $cm^{-1}$ for the associated carboxylic acid salt (—$COO^-$ anti-symmetric stretch) on γ-PGA was observed. The characteristic absorption due to C═O in secondary amides (amide I band) was overlapped by the characteristic peak of —$COO^-$. Additionally, the characteristic peak observed at 3400 $cm^{-1}$ was the N—H stretch of γ-PGA. In the $^1$H-NMR spectrum (FIG. 2*b*), six chief signals were observed at 1.73 and 1.94 ppm (β-$CH_2$), 2.19 ppm (γ-$CH_2$), 4.14 ppm (α-CH), 8.15 ppm (amide), and 12.58 ppm (COOH). These results indicated that the observed FT-IR and $^1$H-NMR spectra correspond well to those expected for γ-PGA. Additionally, the fermented product after purification showed no detected macromolecular impurities by the $^1$H-NMR analysis, suggesting that the obtained white power of γ-PGA is highly pure. The applicable γ-PGA for nanoparticles of the present invention is between about 10 kDa and 100 kDa, preferably between about 20 kDa and 60 kDa.

EXAMPLE NO. 4

Preparation of the CS-γ-PGA Nanoparticles

Nanoparticles were obtained upon addition of γ-PGA aqueous solution (pH 7.4, 2 ml), using a pipette (0.5-5. ml, PLASTIBRAND®, BrandTech Scientific Inc., Germany), into a low-MW CS aqueous solution (pH 6.0, 10 ml) at varying concentrations (0.01%, 0.05%, 0.10%, 0.15%, or 0.20% by w/v) under magnetic stirring at room temperature. Nanoparticles were collected by ultracentrifugation at 38,000 rpm for 1 hour. Supernatants were discarded and nanoparticles were resuspended in deionized water for further studies. FT-IR was used to analyze peak variations of amino groups of low-MW CS and carboxylic acid salts of γ-PGA in the CS-γ-PGA nanoparticles.

Figure 3:
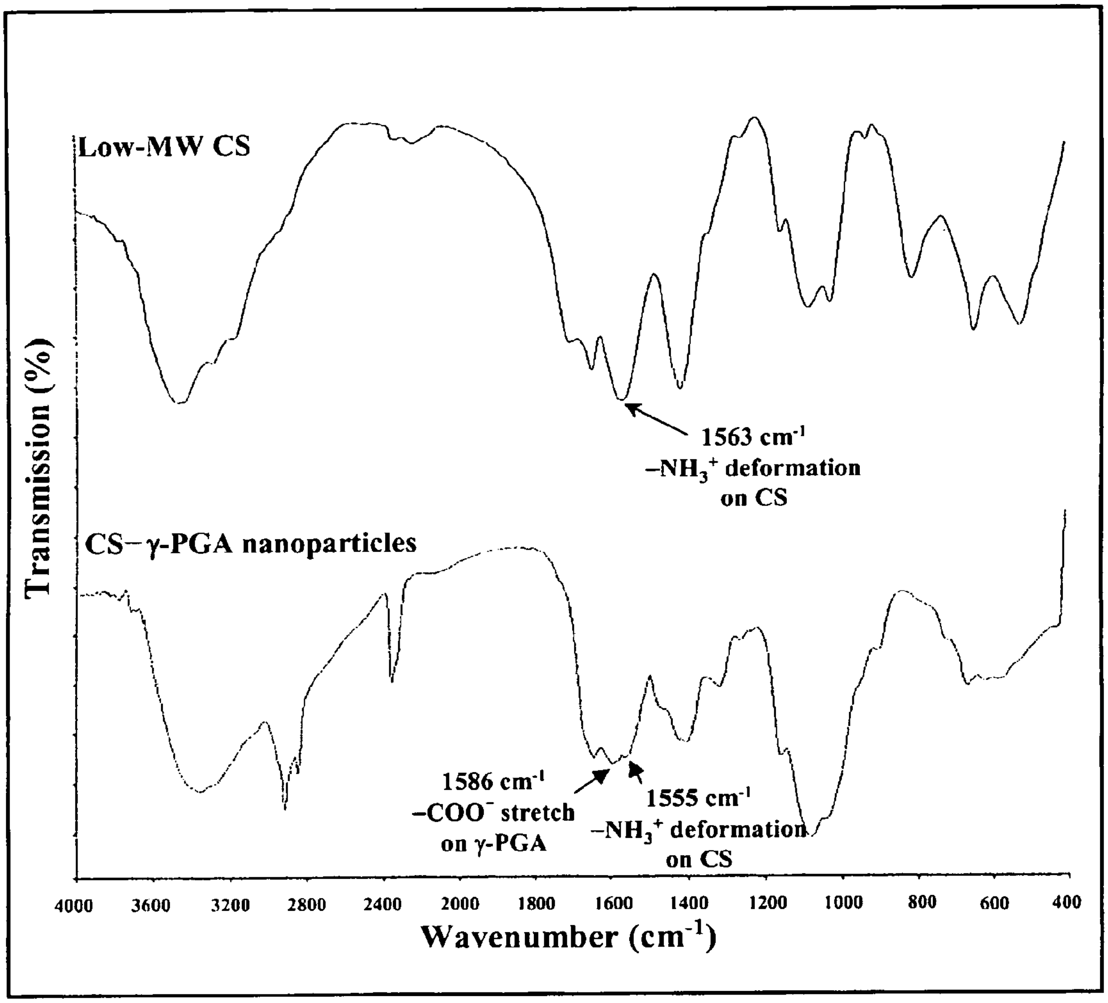
FIG. 3 shows FT-IR spectra of the low-MW CS and the prepared CS-γ-PGA nanoparticles.
Figure 4:
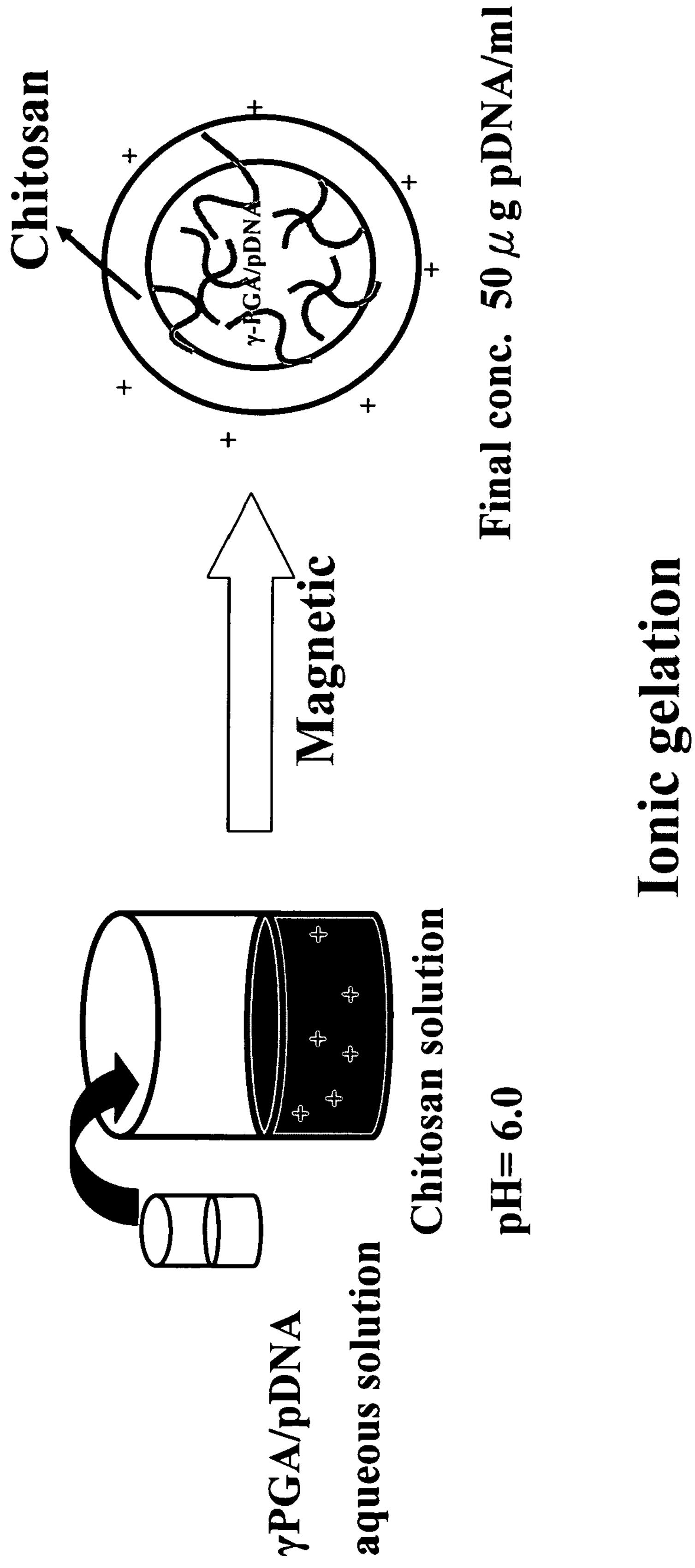
FIG. 4 shows a simple ionic gelation process for nanoparticles manufacturing.

As stated, nanoparticles were obtained instantaneously upon addition of a γ-PGA aqueous solution (pH 7.4) into a low-MW CS aqueous solution (about pH 6.0) under magnetic stirring at room temperature. FIG. 4 shows a simple ionic gelation process for nanoparticles manufacturing. FIG. 3 shows the FT-IR spectra of the low-MW CS and the CS-γ-PGA nanoparticles. As shown in the spectrum of CS, the characteristic peak observed at 1563 $cm^{-1}$ was the protonated amino group (—$NH_3^+$ deformation) on CS. In the spectrum of CS-γ-PGA complex, the characteristic peak at 1615 $cm^{-1}$ for —$COO^-$ on γ-PGA disappeared and a new peak at 1586 $cm^{-1}$ appeared, while the characteristic peak of —$NH_3^+$ deformation on CS at 1563 $cm^{-1}$ shifted to 1555 $cm^{-1}$. These observations are attributed to the electrostatic interaction between the negatively charged carboxylic acid salts (—$COO^-$) on γ-PGA and the positively charged amino groups (–$NH_3^+$) on CS (Int. J. Pharm. 2003;250:215-226). The electrostatic interaction between the two polyelectrolytes (γ-PGA and CS) instantaneously induced the formation of long hydrophobic segments (or at least segments with a high density of neutral ion-pairs), and thus resulted in highly neutralized complexes that segregated into colloidal nanoparticles.

EXAMPLE NO. 5

Characterization of the CS-γ-PGA Nanoparticles

The morphological examination of the CS-γ-PGA nanoparticles was performed by TEM (transmission electron microscopy) and/or AFM (atomic force microscopy). The TEM sample was prepared by placing a drop of the nanoparticle solution onto a 400 mesh copper grid coated with carbon. About 2 minutes after deposition, the grid was tapped with a filter paper to remove surface water and positively stained by using an alkaline bismuth solution (Microbiol. Immunol. 1986;30:1207-1211). The AFM sample was prepared by casting a drop of the nanoparticle solution on a slide glass and then dried in vacuum. The size distribution and zeta potential of the prepared nanoparticles were measured using a Zetasizer (3000HS, Malvem Instruments Ltd., Worcestershire, UK).

During storage, aggregation of nanoparticles may occur and thus leads to losing their2structural integrity or forming precipitation of nanoparticles (Eur. J. Pharm. Sci. 1999;8:99-107). Therefore, the stability of nanoparticles during storage must be evaluated. In the stability study, the prepared nanoparticles suspended in deionized water (1 mg/ml) were stored at 4° C. and their particle sizes and zeta potential values were monitored by the same Zetasizer as mentioned earlier during storage.

In the preparation of nanoparticles, samples were visually analyzed and three distinct solution systems were identified: clear solution, opalescent suspension, and solution with precipitation of aggregates. Examined by the Zetasizer, nanoparticles were found in the clear solution and the opalescent suspension rather than in the solution with precipitation of aggregates.

The particle sizes and the zeta potential values of CS-γ-PGA nanoparticles were determined and the results are shown in Tables 1a and 1b. It was found that the particle size and the zeta potential value of the prepared nanoparticles were mainly determined by the relative amount of the local concentration of γ-PGA in the added solution to the surrounding concentration of CS in the sink solution. At a fixed concentration of CS, an increase in the γ-PGA concentration allowed γ-PGA molecules interacting with more CS molecules, and thus formed a lager size of nanoparticles (Table 1a, $p<0.05$). When the amount of CS molecules exceeded that of local γ-PGA molecules, some of the excessive CS molecules were entangled onto the surfaces of CS-γ-PGA nanoparticles.

Thus, the resulting nanoparticles may display a structure of a neutral polyelectrolyte-complex core surrounded by a positively charged CS shell (Table 1b) ensuring the colloidal stabilization (Langmuir. 2004;20:7766-7778). In contrast, as the amount of local γ-PGA molecules sufficiently exceeded that of surrounding CS molecules, the formed nanoparticles had γ-PGA exposed on the surfaces and thus had a negative charge of zeta potential. Therefore, the particle size and the zeta potential value of the prepared CS-γ-PGA nanoparticles can be controlled by their constituted compositions.

Figure 5:
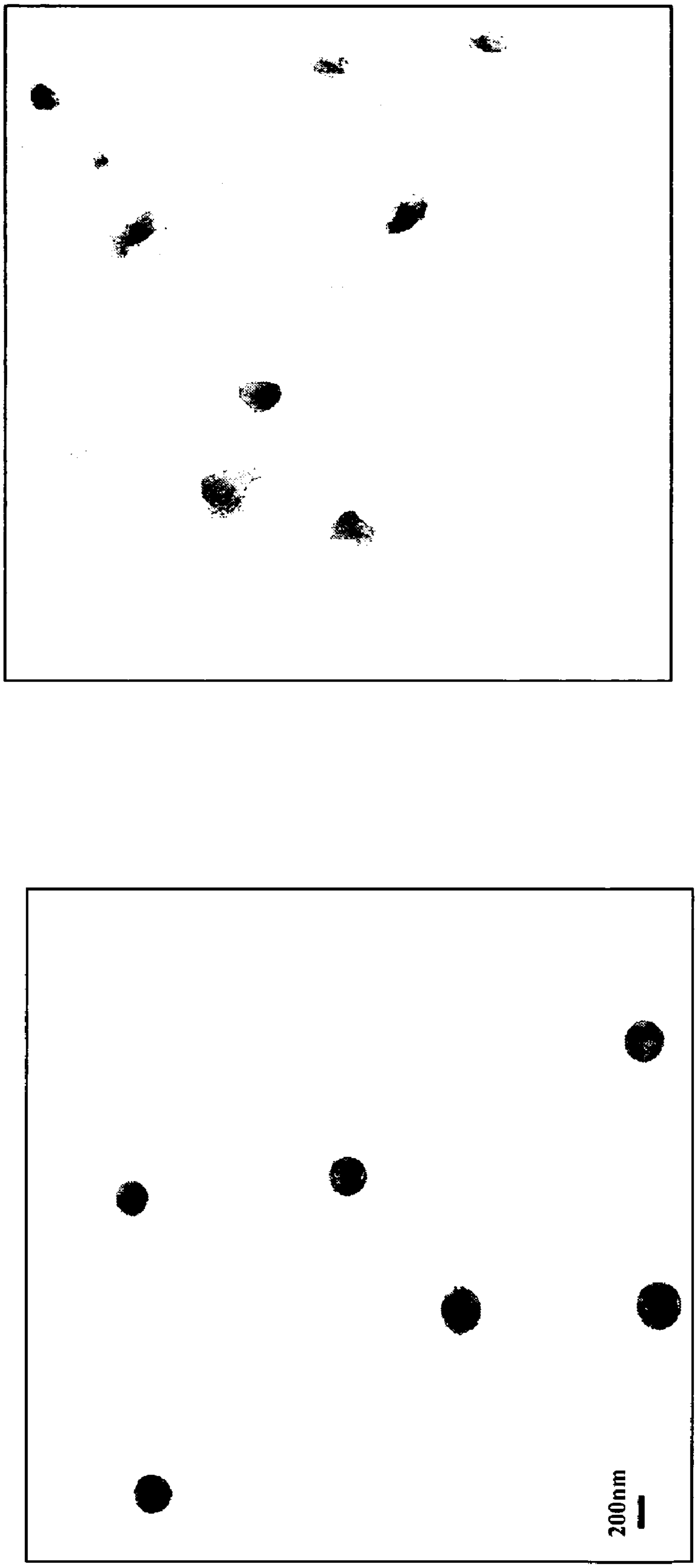
FIG. 5 shows (a) a TEM micrograph of the prepared CS-γ-PGA nanoparticles encapsulated with pDNA and (b) a TEM micrograph of the prepared CS nanoparticles encapsulated with pDNA.
Figure 6:
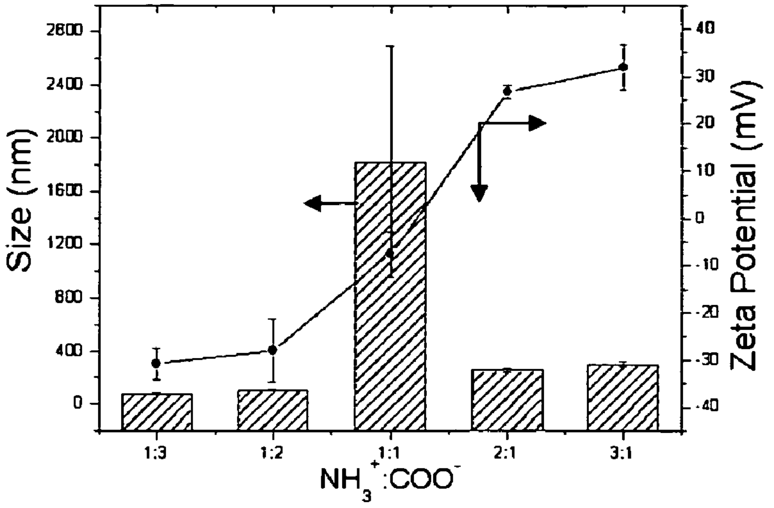
FIG. 6 shows particle size and zeta potential of the CS-γ-PGA nanoparticles encapsulated with pDNA.
Figure 7:
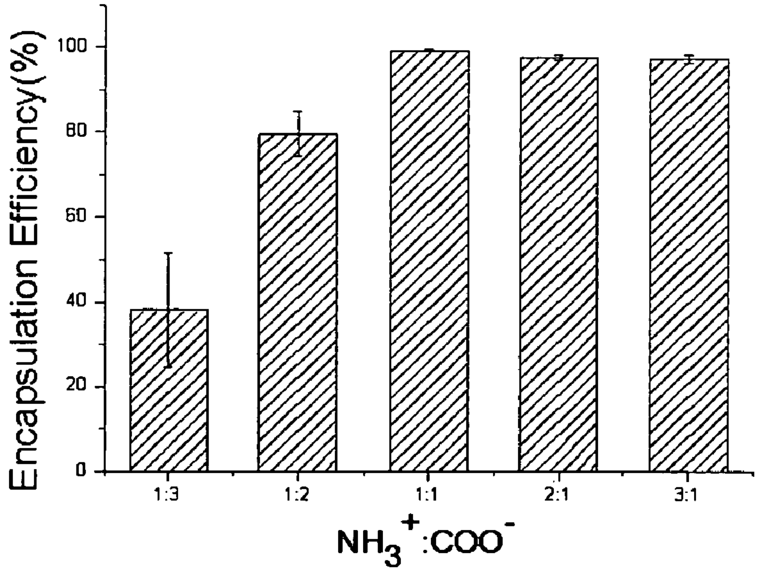
FIG. 7 shows the encapsulation efficiency of the CS-γ-PGA nanoparticles encapsulated with pDNA.

FIG. 5 shows (a) a TEM micrograph of the prepared CS-γ-PGA nanoparticles encapsulated with pDNA and (b) a TEM micrograph of the prepared CS nanoparticles encapsulated with pDNA. CS (+) and γPGA (−) are polyelectrolytes and pDNA was encapsulated when the nanoparticles were formed. The size and zeta potential of the prepared nanoparticles increased with the increase of the ratio of $NH_3^+/COO^-$ (FIG. 6). The encapsulation efficiency of the prepared nanoparticles was less than 90% when the $NH_3^+/COO^-$ ratio was lower than 1 (FIG. 7). Some aspects of the invention relate to nanoparticles for transcutaneous bombardment delivery processes having a mean particle size between about 50 and 500 nanometers, preferably between about 100 and 300 nanometers, and most preferably between about 150 and 250 nanometers. The morphology of the nanoparticles with encapsulated bioactive agents shows spherical in shape with a substantially smooth surface.

TABLE 1a

Effects of concentrations of γ-PGA and CS on the particle sizes of the prepared CS-γ-PGA nanoparticles
Mean Particle Size (nm, n = 5)

| | CS | | | | |
|---|---|---|---|---|---|
| γ-PGA | 0.01% [a)] | 0.05% | 0.10% | 0.15% | 0.20% |
| 0.01% [b)] | 79.0 ± 3.0 | 103.1 ± 4.6 | 96.7 ± 1.9 | 103.6 ± 1.9 | 140.5 ± 2.0 |
| 0.05% | 157.4 ± 1.7 | 120.8 ± 3.9 | 144.5 ± 2.4 | 106.2 ± 3.8 | 165.4 ± 1.7 |
| 0.10% | 202.2 ± 3.1 | 232.6 ± 1.2 | 161.0 ± 1.8 | 143.7 ± 2.7 | 218.1 ± 4.1 |
| 0.15% | 277.7 ± 3.2 | 264.9 ± 2.1 | 188.6 ± 2.9 | 178.0 ± 2.2 | 301.1 ± 6.4 |
| 0.20% | 284.1 ± 2.1 | 402.2 ± 4.0 | ▲ | 225.5 ± 3.1 | 365.5 ± 5.1 |

[a)] concentration of CS (by w/v)
[b)] concentration of γ-PGA (by w/v)
▲ precipitation of aggregates was observed TABLE 1b Effects of concentrations of γ-PGA and CS on the zeta potential values of the prepared CS-γ-PGA nanoparticles.
Zeta Potential (mV, n = 5)

| | CS | | | | |
|---|---|---|---|---|---|
| γ-PGA | 0.01% [a)] | 0.05% | 0.10% | 0.15% | 0.20% |
| 0.01% [b)] | 15.4 ± 0.3 | 22.8 ± 0.5 | 19.8 ± 1.5 | 16.5 ± 1.4 | 17.2 ± 1.6 |
| 0.05% | −32.7 ± 0.7 | 23.7 ± 1.7 | 27.6 ± 0.7 | 20.3 ± 0.8 | 19.2 ± 0.6 |
| 0.10% | −33.1 ± 1.3 | 21.1 ± 1.6 | 20.3 ± 1.1 | 23.6 ± 0.9 | 24.7 ± 1.2 |
| 0.15% | −33.2 ± 2.1 | −21.9 ± 2.0 | 19.2 ± 0.4 | 16.9 ± 1.7 | 19.8 ± 0.3 |
| 0.20% | −34.5 ± 0.5 | −34.6 ± 0.3 | ▲ | 14.6 ± 0.7 | 16.3 ± 0.7 |

[a)] concentration of CS (by w/v)
[b)] concentration of γ-PGA (by w/v)
▲ precipitation of aggregates was observed

EXAMPLE NO. 6

Insulin Loading Capacity in Nanoparticles

The insulin-loaded CS-γPGA nanoparticles are prepared by using the ionic-gelation method upon addition of insulin mixed with γ-PGA solution into CS solution, followed by magnetic-stirring in a container. Model insulin used in the experiment and disclosed herein is obtained from bovine pancreas (Sigma-Aldrich, St. Louis, Mo.), having a molecular formula of $C_{254}H_{377}N_{65}O_{75}S_6$ with a molecular weight of about 5733.5 and an activity of ≧27 USP units/mg. The insulin contains two-chain polypeptide hormone produced by the β-cells of pancreatic islets. The α and β chains are joined by two interchain disulfide bonds. Insulin regulates the cellular uptake, utilization, and storage of glucose, amino acids, and fatty acids and inhibits the breakdown of glycogen, protein, and fat. The insulin from Sigma-Aldrich contains about 0.5% zinc. Separately, insulin can be obtained from other sources, such as human insulin solution that is chemically defined, recombinant from *Saccharomyces cerevisiae*. Some aspects of the invention relate to nanoparticles with insulin in the core, wherein the insulin may contain intermediate-acting, regular insulin, rapid-acting insulin, sustained-acting insulin that provides slower onset and longer duration of activity than regular insulin, or combinations thereof.

Examples of insulin or insulin analog products include, but not limited to, Humulin® (by Eli Lilly), Humalog® (by Eli Lilly) and Lantus® (by Aventis), and Novolog® Mix70/30 (by Novo Nordisk, Denmark). Humalog (insulin lispro, rDNA origin) is a human insulin analog that is a rapid-acting, parenteral blood glucose-lowering agent. Chemically, it is Lys(B28), Pro(B29) human insulin analog, created when the amino acids at positions 28 and 29 on the insulin B-chain are reversed. Humalog is synthesized in a special non-pathogenic laboratory strain of *Escherichia coli* bacteria that has been genetically altered by the addition of the gene for insulin lispro. Humalog has the empirical formula $C_{257}H_{383}N_{65}O_{77}S_6$ and a molecular weight of 5808, identical to that of human insulin. The vials and cartridges contain a sterile solution of Humalog for use as an injection. Humalog injection consists of zinc-insulin lispro crystals dissolved in a clear aqueous fluid. Each milliliter of Humalog injection contains insulin lispro 100 Units, 16 mg glycerin, 1.88 mg dibasic sodium phosphate, 3.15 mg m-cresol, zinc oxide content adjusted to provide 0.0197 mg zinc ion, trace amounts of phenol, and water for injection. Insulin lispro has a pH of 7.0-7.8. Hydrochloric acid 10% and/or sodium hydroxide 10% may be added to adjust pH.

Humulin is used by more than 4 million people with diabetes around the world every day. Despite its name, this insulin does not come from human beings. It is identical in chemical structure to human insulin and is made in a factory using a chemical process called recombinant DNA technology. Humulin L is an amorphous and crystalline suspension of human insulin with a slower onset and a longer duration of activity (up to 24 hours) than regular insulin. Humulin U is a crystalline suspension of human insulin with zinc providing a slower onset and a longer and less intense duration of activity (up to 28 hours) than regular insulin or the intermediate-acting insulins (NPH and Lente).

LANTUS® (insulin glargine [rDNA origin] injection) is a sterile solution of insulin glargine for use as an injection. Insulin glargine is a recombinant human insulin analog that is a long-acting (up to 24-hour duration of action), parenteral blood-glucose-lowering agent. LANTUS is produced by recombinant DNA technology utilizing a non-pathogenic laboratory strain of *Escherichia coli* (K12) as the production organism. Insulin glargine differs from human insulin in that the amino acid asparagine at position A21 is replaced by glycine and two arginines are added to the C-terminus of the B-chain. Chemically, it is $21^A$-Gly-$30^B$a-L-Arg-$30^B$b-L-Arg-human insulin and has the empirical formula $C_{267}H_{404}N_{72}O_{78}S_6$ and a molecular weight of 6063.

LANTUS consists of insulin glargine dissolved in a clear aqueous fluid. Each milliliter of LANTUS (insulin glargine injection) contains 100 IU (3.6378 mg) insulin glargine. Inactive ingredients for the 10 mL vial are 30 mcg zinc, 2.7 mg m-cresol, 20 mg glycerol 85%, 20 mcg polysorbate 20, and water for injection. Inactive ingredients for the 3 mL cartridge are 30 mcg zinc, 2.7 mg m-cresol, 20 mg glycerol 85%, and water for injection.

Novolog® Mix70/30 (70% insulin as part protamine suspension and 30% insulin aspart injection [rDNA origin]) is a human insulin analog suspension. Novolog® Mix70/30 is a blood glucose-lowering agent with a rapid onset and an intermediate duration of action. Insulin aspart is homologous with regular human insulin with the exception of a single substitution of the amino acid praline by aspartic acid in position B28, and is produced by recombinant DNA technology utilizing *Saccharomyces cerevisiae* as the production organism. Insulin aspart (Novolog) has the empirical formula $C_{256}H_{381}N_{65}O_{79}S_6$ and a molecular weight of 5826. Novolog® Mix70/30 is a uniform, white sterile suspension that contains zinc 19.6 μg/ml and other components.

The nanoparticles with two insulin concentrations (at 0.042 and 0.083 mg/ml, respectively) are prepared at a chitosan to γ-PGA ratio of 0.75 mg/ml to 0.167 mg/ml. Their particle size and zeta potential are shown in Table 2 below.

TABLE 2

| Insulin Conc. (mg/ml)(n = 5) | Mean Particle Size (nm) | Polydispersity Index (PI) | Zeta Potential (mV) |
|---|---|---|---|
| 0* | 145.6 ± 1.9 | 0.14 ± 0.01 | +32.11 ± 1.61 |
| 0.042 | 185.1 ± 5.6 | 0.31 ± 0.05 | +29.91 ± 1.02 |
| 0.083 | 198.4 ± 6.2 | 0.30 ± 0.09 | +27.83 ± 1.22 |

*control reference without insulin

Figure 8:
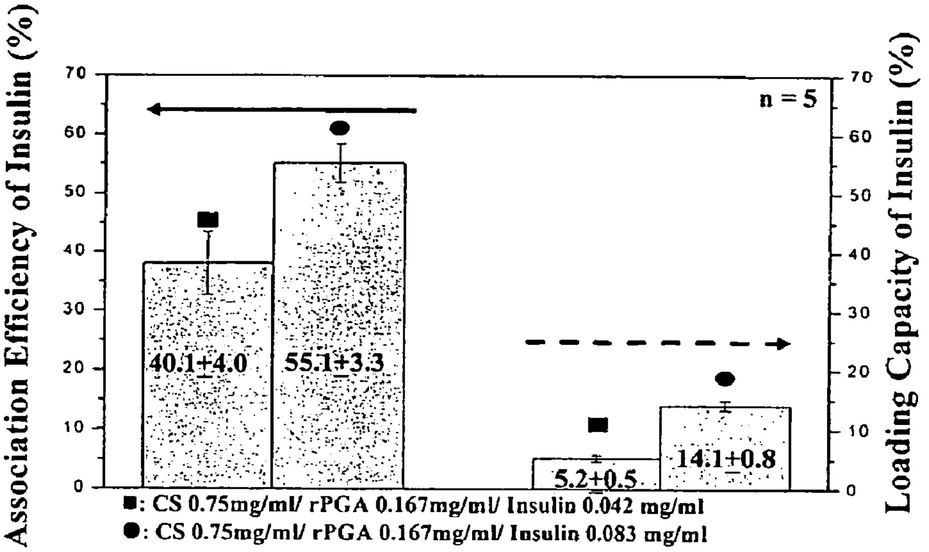
FIG. 8 shows loading capacity and association efficiency of insulin in nanoparticles of chitosan and γ-PGA.
Figure 9:
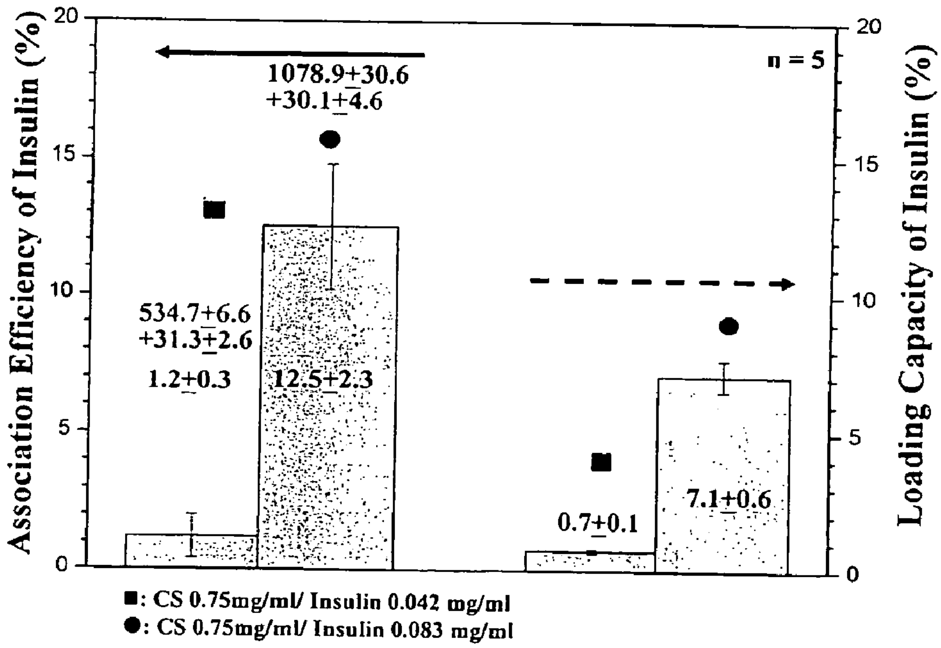
FIG. 9 shows loading capacity and association efficiency of insulin in nanoparticles of chitosan as reference.

Further, their association efficiency of insulin and loading capacity of insulin are analyzed, calculated and shown in FIGS. 8 and 9, according to the following formula:

$$\text{Insulin Association Efficiency}(AE\,\%) = \frac{\left(\begin{array}{c}\text{Total amount of insulin} - \\ \text{Insulin in supernatant}\end{array}\right)}{\text{Total amount of insulin}} \times 100\,\%$$

$$\text{Loading Capacity}\,(LC) = \frac{\left(\begin{array}{c}\text{Total amount of insulin} - \\ \text{Insulin in supernatant}\end{array}\right)}{\text{Weight of recovered particles}} \times 100\,\%$$

FIG. 8 shows loading capacity and association efficiency of insulin in nanoparticles made of interacted chitosan and γ-PGA, whereas FIG. 9 shows loading capacity and association efficiency of insulin in nanoparticles made of chitosan alone (in the absence of γ-PGA) as reference. The data clearly demonstrates that both the insulin loading capacity and insulin association efficiency are statistically higher for the nanoparticles with γ-PGA or a polyanionic compound in the core. The AE (40~55%) and LC (5.0~14.0%) of insulin for CS-γPGA nanoparticles was obtained by using ionic-gelation method upon addition of insulin mixed with γ-PGA solution into CS solution, followed by magnetic stirring for nanoparticle separation.

Some aspects of the invention relate to nanoparticles comprising a polyanionic component (such as γ-PGA, α-PGA, PGA derivatives, heparin, heparin analogs, low molecular weight heparin, glycosaminoglycans, or alginate) in the core and low molecular weight chitosan in the shell, wherein the chitosan dominates on a surface of the nanoparticles with surface positive charges. In use, firstly, encapsulate the Alzheimer's drug in the chitosan shell nanoparticle as described herein, wherein the nanoparticle is partially crosslinked (optionally) to enhance its biodurability. Then transcutaneously topical administer the nanoparticles via a nanoparticle nanoprojectile bombardment process, whereby the nanoparticles migrate to the brain via capillary and artery circulation. The chitosan shell of certain intact nanoparticles adheres to the surface adjacent the tight junction in the brain. Thereafter, the chitosan nanoparticle opens the tight junction, wherein the Alzheimer's drug is released after passing the tight junction for therapeutic treatment. In one embodiment, the nanoparticles are in a spherical shape having a mean particle size of about 50 to 250 nanometers, preferably 150 nanometers to 250 nanometers.

In one example, transcutaneous topical administration of the nanoparticles comprising chitosan shell substrate, polyanionic core substrate and at least one bioactive agent for treating Alzheimer's disease in a patient is typically performed with about 5 mg to 100 mg, preferably about 10 to 40 mg, of active agent per day over a period of one month to one year. The bioactive agent is selected from a group consisting of donepezile, rivastignine, galantamine, and/or those trade-named products, such as memantine hydrochloride (Axura® by Merz Pharmaceuticals), donepezil hydrochloride (Aricept® by Eisai Co. Ltd.), rivastigmine tartrate (Exelon® by Novartis), galantamine hydrochloride (Reminyl® by Johnson & Johnson), and tacrine hydrochloride (Cognex® by Parke Davis).

Some aspects of the invention relate to a nanoparticle with a core substrate comprising polyglutamic acids such as water soluble salt of polyglutamic acids (for example, ammonium salt) or metal salts of polyglutamic acid (for example, lithium salt, sodium salt, potassium salt, magnesium salt, and the like). In one embodiment, the form of polyglutamic acid may be selected from a group consisting of poly-α-glutamic acid, poly-L-α-glutamic acid, poly-γ-glutamic acid, poly-D- glutamic acid, poly-γ-D-glutamic acid, poly-γ-DL-glutamic acid, poly-L-glutamic acid (manufactured by Sigma-Aldrich, St. Louis, Mo.), and PEG or PHEG derivatives of poly-glutamic acid. Alginate is generally non-biodegradable; however, it is stipulated that an alginate particle with about 30-50 kDa molecular weight is kidney inert. Heparin with negatively charged side-groups has a general chemical structure as shown below:

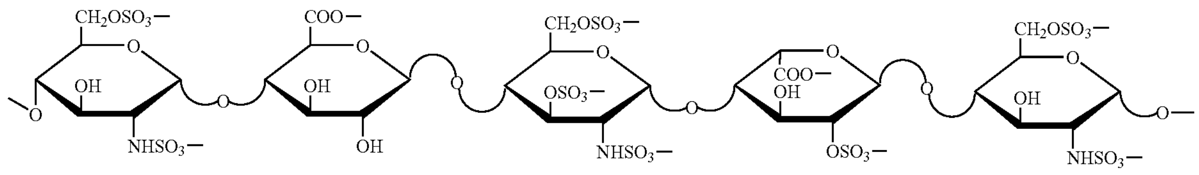

Some aspects of the invention relate to the negatively charged glycosaminoglycans (GAGs) as the core substrate of the present nanoparticle formulation. GAGs may be used to complex with a low-molecular-weight chitosan to form drug-carrier nanoparticles. GAGs may also conjugate with the protein drugs or bioactive agents (including DNA and genes) as disclosed herein to enhance the bonding efficiency of the core substrate in the nanoparticles. Particularly, the negatively charged core substrate (such as GAGs, heparin, PGA, alginate, and the like) of the nanoparticles of the present invention may conjugate with chondroitin sulfate, hyaluronic acid, PDGF-BB, BSA, EGF, MK, VEGF, KGF, bFGF, aFGF, MK, PTN, etc.

EXAMPLE NO. 7

Insulin Nanoparticle Stability

Figure 10:
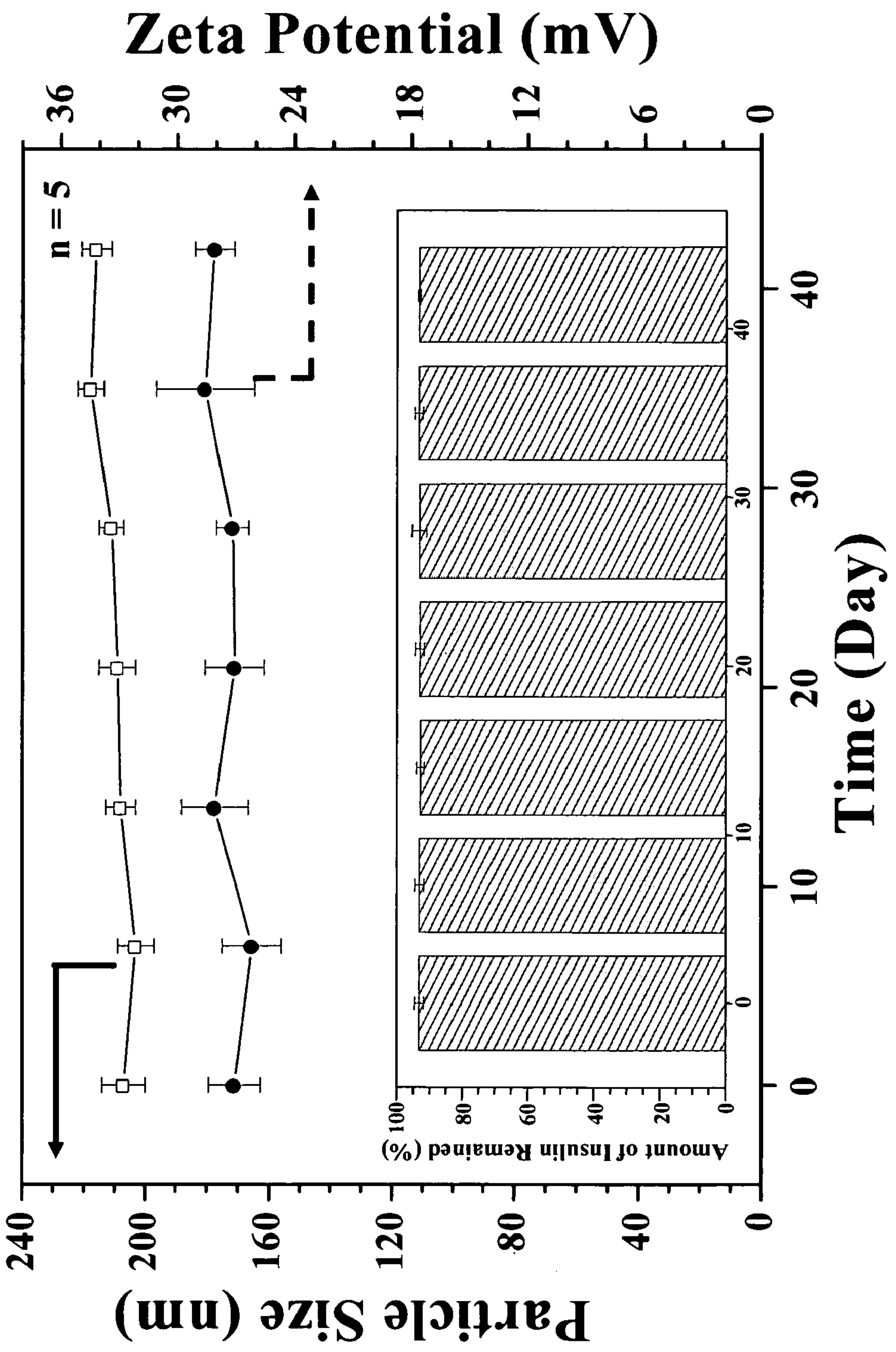
FIG. 10 shows the stability of insulin-loaded nanoparticles.

FIG. 10 shows the stability of insulin-loaded nanoparticles of the present invention with an exemplary composition of CS 0.75 mg/ml, γ-PGA 0.167 mg/ml, and insulin 0.083 mg/ml in the manufacturing process. The prepared insulin-loaded nanoparticles suspended in deionized water are stable during storage up to 40 days. Firstly (in FIG. 10), the insulin content in the nanoparticle storage solution maintains at about a constant level of 9.5%. The nanoparticle stability is further evidenced by the substantially constant particle size at about 200 nm and substantially constant zeta potential of about +28 mV over the period of about 40 days. It is contemplated that the insulin-containing nanoparticles of the present invention would further maintain their biostability when formulated in a soft gelcap configuration that further isolates the nanoparticles from environmental effects, such as sunlight, heat, air conditions, contaminants, and the like. Some aspects of the invention provide a gelcap pill containing a dosage of insulin nanoparticles effective amount of the insulin to treat or manage the diabetic patients, wherein the stability of the insulin-containing nanoparticles is at least 40 days, preferably more than 6 months, and most preferably more than a couple of years. By "effective amount of the insulin", it is meant that a sufficient amount of insulin will be present in the dose to provide for a desired therapeutic, prophylatic, or other biological effect when the compositions are administered to a host in the single dosage forms.

EXAMPLE NO. 8

In Vivo Study with Insulin-Loaded Fluorescence-Labeled Nanoparticles

In the in vivo study, rats were injected with streptozotocin (STZ 75 mg/kg intraperitoneal) in 0.01M citrate buffer (pH 4.3) to induce diabetes rats. The blood from the rat's tail was analyzed with a commercially available glucometer for blood glucose. The blood glucose level on Wistar male rats at no fasting (n=5) is measured at 107.2±8.1 mg/dL for normal rats while the blood glucose level is at 469.7±34.2 mg/dL for diabetic rats. In the animal study, diabetic rats were fasting for 12 hours and subjected to four different conditions: (a) oral deionized water (DI): administration; (b) oral insulin administration at 30 U/kg; (c) oral insulin-loaded nanoparticles administration at 30 U/kg; and (d) subcutaneous (SC) insulin injection at 5 U/kg as positive control. The blood glucose concentration from rat's tail was measured over the time in the study.

Figure 11:
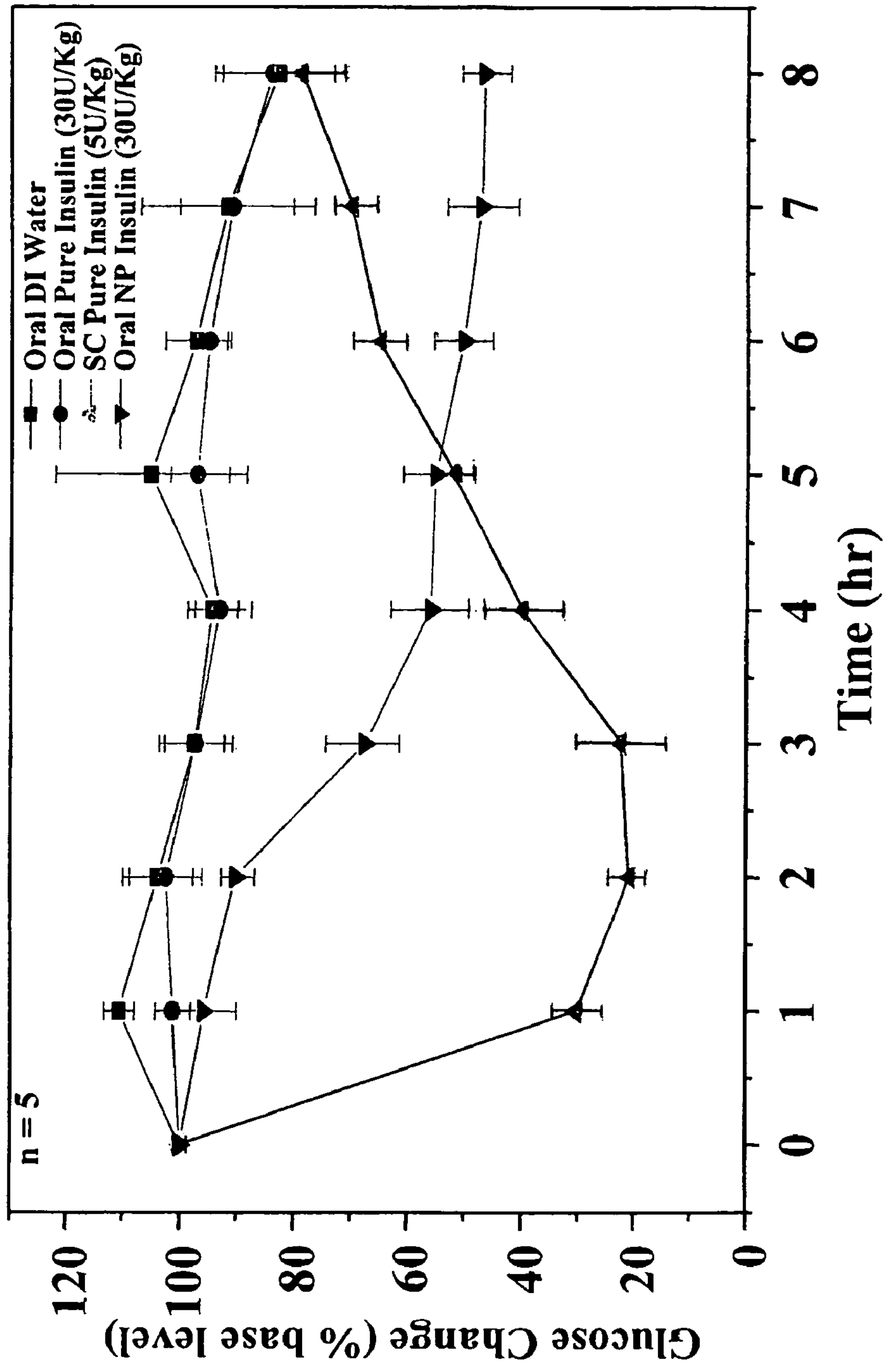
FIG. 11 shows the bioavailability of insulin of administered insulin-loaded nanoparticles in diabetic rats.

FIG. 11 shows glucose change (hypoglycemic index) versus time of the in vivo animal study (n=5). The glucose change as a percentage of base lines for both oral DI administration and oral insulin administration over a time interval of 8 hours appears relatively constant within the experimental measurement error range. It is illustrative that substantially all insulin from the oral administration route has been decomposed in rat stomach. As anticipated, the glucose decrease for the SC insulin injection route appears in rat blood in the very early time interval and starts to taper off after 3 hours in this exemplary study. The most important observation of the study comes from the oral administration route with insulin-loaded nanoparticles. The blood glucose begins to decrease from the base line at about 2 hours after administration and sustains at a lower glucose level at more than 8 hours into study. Regarding oral administration route with insulin-loaded nanoparticles of the present invention, several repeated rat insulin studies (not shown here) confirmed sustained effects of lower glucose levels for up to 24 hours. It suggests that the current insulin-loaded nanoparticles modulate the glucose level in animals in a sustained or prolonged effective mode.

Some aspects of the invention relate to a novel nanoparticle system that is composed of a low-MW CS and γ-PGA with CS dominated on the surfaces. The surface of the nanoparticles is characterized with a positive surface charge. In one embodiment, the nanoparticles of the invention enables effective delivery for bioactive agent, including peptide, polypeptide, protein drugs, other large hydrophilic molecules, DNA, genes, and the like. Such polypeptide drugs can be any natural or synthetic polypeptide that may be administered to a human patient. Exemplary drugs include, but are not limited to, insulin; growth factors, such as epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; somatostatin; somatotropin; somatropin; somatrem; calcitonin; parathyroid hormone; colony stimulating factors (CSF); clotting factors; tumor necrosis factors: interferons; interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; LHRH; GHRH; tissue plasminogen activators; macrophage activator; chorionic gonadotropin; heparin; atrial natriuretic peptide; hemoglobin; retroviral vectors; relaxin; cyclosporin; oxytocin; vaccines; monoclonal antibodies; and the like; and analogs and derivatives of these compounds. The bioactive agent of the present invention may be selected from group consisting of oxytocin, vasopressin, adrenocorticotrophic hormone, prolactin, luliberin or luteinising hormone releasing hormone, growth hormone, growth hormone releasing factor, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines.

EXAMPLE NO. 9

Nanoparticles with Complexed Calcitonin

Calcitonin is a protein drug that serves therapeutically as calcium regulators for treating osteoporosis (J. Pharm. Pharmacol. 1994;46:547-552). Calcitonin has a molecular formula of $C_{145}H_{240}N_{44}O_{48}S_2$ with a molecular weight of about 3431.9 and an isoelectric point of 8.7. The net charge for calcitonin at pH7.4 is positive that is suitable to complex or conjugate with negatively charged core substrate, such as γ-PGA or α-PGA. In preparation, nanoparticles were obtained upon addition of a mixture of γ-PGA plus calcitonin aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) at concentrations higher than 0. 10% by w/v under magnetic stirring at room temperature to ensure positive surface charge. Nanoparticles were collected by ultracentrifugation at 38,000 rpm for 1 hour. Supernatants were discarded and nanoparticles were resuspended in deionized water as the solution products, further encapsulated in soft gels or further treated with an enteric coating. Nanoparticles with complexed calcitonin or other calcium regulators for treating osteoporosis appears a candidate for transcutaneous administration to a patient via the suggested nanoparticle projectile bombardment route as discussed herein.

EXAMPLE NO. 10

Nanoparticles with Conjugated Vancomycin

Vancomycin is a protein drug that serves therapeutically as antibiotic against bacterial pathogens. Vancomycin has a molecular formula of $C_{66}H_{75}N_9O_{24}$ with a molecular weight of about 1485.7 and an isoelectric point of 5.0. The net charge for vancomycin at pH7.4 is negative that is suitable to complex or conjugate with a portion of negatively charged shell substrate, such as chitosan. In preparation, nanoparticles were obtained upon addition of a mixture of γ-PGA plus vancomycin aqueous solution (pH 7.4, 2 ml), using a pipette (0.5-5 ml, PLASTIBRAND®, BrandTech Scientific Inc., Germany), into a low-MW CS aqueous solution (pH 6.0, 10 ml) with excess concentrations under magnetic stirring at room temperature, wherein CS concentration is provided sufficiently to conjugate vancomycin, to counterbalance γ-PGA, and exhibit positive surface charge for the nanoparticles with excess non-conjugated CS. Nanoparticles were collected by ultracentrifugation at 38,000 rpm for 1 hour. Supernatants were discarded and nanoparticles were resuspended in deionized water as the solution products, further encapsulated in soft gels or further treated with an enteric coating. Nanoparticles with conjugated vancomycin or other antibiotics appears a candidate for transcutaneous administration to a patient via the suggested nanoparticle projectile bombardment gun route as discussed herein.

Some aspects of the invention relate to a method of delivering at least one bioactive agent to a patient comprising administering nanoparticles composed chitosan (or of γ-PGA and chitosan) via topical transcutaneous or targeted epidermal/transdermal routes using a nanoparticle bombardment gun, wherein the nanoparticles are loaded with a therapeutically effective amount or dose of the at least one bioactive agent. In a preferred embodiment, the nanoparticles are biodegradable. In another embodiment, the nanoparticles are made of biodegradable polymer selected from a group consisting of poly(L-lactic acid), polyglycolic acid, poly (D,L-lactide-co-glycolide), poly (ester amides), polycaprolactone, co-polymers thereof, and the like. The biodegradable polymer comprises a biodegradable linkage selected from the group consisting of ether groups, ester groups, carbonate groups, amide groups, anhydride groups, and orthoester groups. By way of example, poly(ester amides), particularly poly[(8-L-Leu-6)$_3$-(8-L-Lys(Bz))$_1$], is well known to one skilled in the art that has been disclosed in U.S. Pat. No. 5,485,496 and elsewhere. Suitable biodegradable polymer to be used in the present invention can be found in Handbook of Biodegradable Polymers by Domb et al. (Harwood Academic Publishers: Amsterdam, The Netherlands 1997). Preferably the materials have been approved by the U.S. Food and Drug Administration.

The nanoparticle of the present invention is an effective delivery system for peptide and protein drugs and other hydrophilic molecules. In a further embodiment, the bioactive agent is selected from the group consisting of proteins, peptides, nucleosides, nucleotides, antiviral agents, antineoplastic agents, antibiotics, and anti-inflammatory drugs. In a further embodiment, the bioactive agent is selected from the group consisting of calcitonin, cyclosporin, insulin, oxytocin, tyrosine, enkephalin, tyrotropin releasing hormone (TRH), follicle stimulating hormone (FSH), luteinizing hormone (LH), vasopressin and vasopressin analogs, catalase, superoxide dismutase, interleukin-II (IL2), interferon, colony stimulating factor (CSF), tumor necrosis factor (TNF) and melanocyte-stimulating hormone. In a further embodiment, the bioactive agent is an Alzheimer antagonist. In another embodiment, the bioactive agent is a gene or a DNA.

EXAMPLE NO. 11

Nanoparticles with Heparin Core Substrate

Heparin is a negatively charged drug that serves therapeutically as anti-coagulant. Heparin is generally administered by intravenous injection. Some aspects of the invention relate to heparin nanoparticles for topical administration or subcutaneous/transcutaneous administration using a nanoparticle projectile bombardment gun. In a further embodiment, heparin serves as at least a portion of the core substrate with chitosan as shell substrate, wherein heparin conjugates with at least one bioactive agent as disclosed herein. In preparation, nanoparticles were obtained upon addition of heparin Leo aqueous solution (2 ml), using a pipette (0.5-5 ml, PLASTIBRAND®, BrandTech Scientific Inc., Germany), into a low-MW CS aqueous solution (pH 6.0, 10 ml) with excess concentrations under magnetic stirring at room temperature.

Nanoparticles were collected by ultracentrifugation at 38,000 rpm for 1 hour. Table 3 shows the conditions of solution preparation and the average nanoparticle size.

TABLE 3

| Conditions | Heparin conc. @2 ml | Chitosan conc. @10 ml | Particle size (nm) |
|---|---|---|---|
| A | 200 iu/ml | 0.09% | 298.2 ± 9.3 |
| B | 100 iu/ml | 0.09% | 229.1 ± 4.5 |
| C | 50 iu/ml | 0.09% | 168.6 ± 1.7 |
| D | 25 iu/ml | 0.09% | 140.1 ± 2.3 |

To evaluate the pH stability of the heparin-containing nanoparticles from Example no. 11, the nanoparticles from Condition D in Table 3 are subjected to various pH for 2 hours (sample size=7). Table 4 shows the average size, size distribution (polydispersity index: PI) and zeta potential (Zeta) of the nanoparticles at the end of 2 hours under various pH environments. The data shows that the nanoparticles are relatively stable. In one embodiment, the nanoparticles of the present invention may include heparin, heparin sulfate, small molecular weight heparin, and heparin derivatives.

TABLE 4

| pH | 1.5 | 2.6 | 6.6 | 7.4 | Deionized water @5.9 |
|---|---|---|---|---|---|
| Size (nm) | 150 ± 9 | 160 ± 12 | 153 ± 2 | 154 ± 4 | 147 ± 5 |
| PI | 0.54 ± 0.03 | 0.50 ± 0.04 | 0.08 ± 0.02 | 0.32 ± 0.03 | 0.37 ± 0.02 |
| Zeta (+) | 15 ± 2 | 33 ± 6 | 15 ± 0.1 | 11 ± 0.2 | 18 ± 4 |

In a further embodiment, a growth factor such as bFGF with pharmaceutically effective amount is added to heparin Leo aqueous solution before the pipetting step in Example No. 11. In our laboratory, growth factors and proteins with pharmaceutically effective amount have been conjugated with heparin to form nanoparticles of the present invention with chitosan as the shell substrate, wherein the growth factor is selected from the group consisting of Vascular Endothelial Growth Factor (VEGF), Vascular Endothelial Growth Factor 2 (VEGF2), basic Fibroblast Growth Factor (bFGF), Vascular Endothelial Growth Factor 121 (VEGF121), Vascular Endothelial Growth Factor 165 (VEGF165), Vascular Endothelial Growth Factor 189 (VEGF189), Vascular Endothelial Growth Factor 206 (VEGF206), Platelet Derived Growth Factor (PDGF), Platelet Derived Angiogenesis Factor (PDAF), Transforming Growth Factor-β (TGF-β), Transforming Growth Factor-α (TGF-α), Platelet Derived Epidermal Growth Factor (PDEGF), Platelet Derived Wound Healing Formula (PDWHF), epidermal growth factor, insulin-like growth factor, acidic Fibroblast Growth Factor (aFGF), human growth factor, and combinations thereof; and the protein is selected from the group consisting of haemagglutinin (HBHA), Pleiotrophin, buffalo seminal plasma proteins, and combinations thereof.

In a co-pending application, U.S. patent application Ser. No. 10/916,170 filed Aug. 11, 2004, it is disclosed that a biomaterial with free amino groups of lysine, hydroxylysine, or arginine residues within biologic tissues is crosslinkable with genipin, a crosslinker (Biomaterials 1999;20:1759-72). It is also disclosed that the crosslinkable biomaterial may be crosslinked with a crosslinking agent or with light, such as ultraviolet irradiation, wherein the crosslinkable biomaterial may be selected from the group consisting of collagen, gelatin, elastin, chitosan, NOCC (N, O, carboxylmethyl chitosan), fibrin glue, biological sealant, and the like. Further, it is disclosed that a crosslinking agent may be selected from the group consisting of genipin, its derivatives, analog (for example, aglycon geniposidic acid), stereoisomers and mixtures thereof. In one embodiment, the crosslinking agent may further be selected from the group consisting of epoxy compounds, dialdehyde starch, glutaraldehyde, formaldehyde, dimethyl suberimidate, carbodiimides, succinimidyls, diisocyanates, acyl azide, reuterin, ultraviolet irradiation, dehydrothermal treatment, tris(hydroxymethyl)phosphine, ascorbate-copper, glucose-lysine and photo-oxidizers, and the like.

In one embodiment, it is disclosed that loading drug onto a chitosan-containing biological material crosslinked with genipin or other crosslinking agent may be used as biocompatible drug carriers for drug slow-release or sustained release. Several biocompatible plastic polymers or synthetic polymers have one or more amine group in their chemical structures, for example poly(amides) or poly(ester amides). The amine group may become reactive toward a crosslinking agent, such as glutaraldehyde, genipin or epoxy compounds of the present invention. In one embodiment, the nanoparticles comprised of crosslinkable biomaterial is crosslinked, for example up to about 50% degree or more of crosslinking, preferably about 1 to about 20% degree of crosslinking of the crosslinkable components of the biomaterial, enabling sustained biodegradation of the biomaterial and/or sustained drug release.

By modifying the chitosan structure to alter its charge characteristics, such as grafting the chitosan with methyl, alkyl (for example, ethyl, propyl, butyl, isobutyl, etc.), polyethylene glycol (PEG), or heparin (including low molecular weight heparin, regular molecular weight heparin, and genetically modified heparin), the surface charge density (zeta potential) of the CS-γPGA nanoparticles-may become more pH resistant or hydrophilic.

Nanoparticles for Transcutaneous Bombardment Delivery

Nanoparticles composed of chitosan (CS) and polyglutamic acid, such as γ-polyglutamic acid (γPGA) or α-polyglutamic acid (αPGA), were prepared by ionotropic gelation to evaluate the topical application of CS-based nanoparticles containing pDNA as a potential approach to genetic immunization using a nanoparticle projectile bombardment gun or a conventional gene gun. In one embodiment, the obtained TEM micrographs showed that CS/γPGA nanoparticles encapsulated with pDNA had a spherical morphology (FIG. 5). In the animal study, CS/γ-PGA nanoparticles encapsulated with pDNA bombarded with a gene gun successfully penetrated the skin of a mouse model and EGFP (i.e., enhanced green fluorescent protein) was expressed. The results support that CS/PGA nanoparticles can substitute gold particles as a DNA carrier. The disadvantages of the conventional DNA coated gold particles via a gene gun approach include: (1) The DNA is coated on surface of a gold particle and the coated DNA may subject to attrition or reduced efficiency due to surface contact with other media during the delivery phase; (2) non-biodegradable gold particles; (3) lack of the ability of controlled release; and (4) high operating pressure using a conventional gene gun. On the contrary, the DNA or bioactive agent is encapsulated in nanoparticles of the present invention to preserve its efficacy, bioavailability, and biodurability with biodegradability of sustained release capability.

Nanoparticle Preparation for Targeted Epidermal Delivery

Nanoparticles encapsulated with pDNA (pEFGP-N2) were produced by ionotropic gelation (FIG. 4). Briefly, γPGA solution was mixed with pDNA and added into a CS solution in various $NH_3^+/COO^-$ ratios under gentle stirring at room temperature. The size and zeta potential of the prepared nanoparticles were measured using a Zetasizer (3000HS, Malvern Instruments Ltd., Worcestershire, UK). The encapsulation efficiency of the nanoparticles was analyzed. Furthermore, the morphology of the prepared nanoparticles was examined by transmission electron microscopy (TEM) as shown in FIG. 5.

EXAMPLE NO. 12

Animal Feasibility Study

Balb/C mice (male, 10-12 weeks old) were used for the animal study. After removing the hair covering the abdomen, the skins were bombarded by selected nanoparticle (encapsulated with pDNA) solutions using a gene gun (Sodnlin, Taiwan). After 24 hours, the mice were sacrificed and the skins were collected. EGFP expression was observed using an inversed confocal laser scanning microscope (CLSM, TCS SL, Leica, Germany). To measure the penetration depth of the nanoparticles, FITC-labeled nanoparticle solutions were loaded in the gene gun and bombarded. After 1 hour, the mice were sacrificed and the bombarded abdomen skins were collected and evaluated using CLSM.

After FITC-labeled CS nanoparticles were bombarded via a gene gun into the skin, they were clearly observed by CLSM at 40-80 μm depth into the skin. This indicated that the prepared nanoparticles are able to penetrate the skin of mice. Additionally, green fluorescence of EGFP was present in the skin layer of mice, after 24 hours of bombardment of the nanoparticles encapsulated with pDNA in the animal study.

Conventional Gene Gun

In general, "Gene gun" is a device that delivers DNA to cells by microprojectile bombardment with extremely high speed delivery. The Helios® Gene Gun has been a new way for in vivo transformation of cells or organisms (i.e. gene therapy, genetic immunization, or DNA vaccination). This gun uses Biolistic® particle bombardment where DNA- or RNA-coated gold particles are loaded into the gun and one pulls the trigger for delivery. A high pressure helium pulse delivers the coated gold particles into virtually any target cell or tissue. The particles carry the DNA so that one does not have to remove cells from tissue in order to transform the cells. One model of the Helios gene gun system, 220-240 V, is used for biolistic particle delivery of biomaterials into cells. This handheld device employs an adjustable helium pulse to sweep DNA-, RNA-, and other biomaterial-coated gold microcarriers from the inner wall of a small plastic cartridge directly into target cells. This system has a 2 square-centimeter target area, and uses a pressure range of 100-600 psi. The system includes the Helios gene gun, helium hose assembly, helium regulator, tubing prep station, syringe kit, tubing cutter, and Helios gene gun optimization kit. Dimensions are 20×25 cm (manufactured by Bio-Rad, Hercules, Calif.). The gene gun is a device for injecting cells with genetic information, originally designed for plant transformation. The payload is an elemental particle of a heavy metal coated with plasmid DNA. The actual name of the gene gun is the Biolistic Particle Delivery System, and this technique is often simply referred to as "biolistics"—a cross between biology and ballistics.

In some aspects, another model of the gene gun consists of two small 6"×7"×10" stainless steel: chambers connected to a 2 HP vacuum pump. When the technician flicks the switch on the outside of the second chamber, helium is released at up to 1000 psi. The blast ruptures a first disk about the size of a nickel. The explosion of the first disk releases a shock wave which travels 1 centimeter until it hits a second disk, which is free to move. Attached to the front of that second disk are microscopic tungsten or gold particles 1 micron in diameter coated with thousands of DNA molecules. This second disk travels another centimeter at the speed of a rifle bullet, for example about 1300 feet per second, and hits a screen, which detains the second disk, but launches the microscopic particles toward the target cells. The particles penetrate the cells and release the DNA, which is diffused into the nucleus and incorporated by the chromosomes of the plant. One very common way of introducing DNA into plant cells is through DNA coated particles (e.g. one micron gold particles) that are literally shot through the cell wall. The gene gun was originally a nail gun for concrete surfaces modified to fire tungsten particles. Later the design was greatly refined. Improvements include the use of helium propellant and a multi-disk-collision delivery mechanism. Other heavy metals such as gold and silver are also used, but not as frequently due to reasons of availability and cost. The gene gun is very useful in applications such as transfaction in agriculture, gene therapy or gene vaccine.

Another model of microprojectile bombardment gun is the "Cloning Gun™" that is a cordless, rechargeable, hand-held electroporation instrument. A cloning gun generally achieves transfection efficiencies exceeding 50% of viable cells with a variety of standard mammalian cell lines.

Nanonarticle Bombardment Gun

The nanoparticle bombardment gun ("NBG gun") may be modified from a conventional gene gun in that the NBG gun operates at a lower pressure of helium sources (in the range of less than 100 psi, preferably less than 80 psi, and most preferably less than 50 psi) for propelling the nanoparticles (in the range of about 50 to 500 nanometers, preferably in the range of 100 to 300 nanometers, and most preferably in the range of 150 to 250 nanometers) that are made of non-metallic material (preferably biodegradable material) instead of metals, such as gold, silver or tungsten. The nanoparticle bombardment gun uses neither a needle nor any sharp object to penetrate into the skin. Nevertheless, the nanoparticle exit-end of the NBG gun is usually placed against the skin for targeted epidermal delivery. In one embodiment, the NBG gun consists of a solenoid valve with NPT female fittings. On the input side, the solenoid is attached to a tubing to connect to the helium regulator; on the other side, it is attached to a filter holder which acts as the support to load the nanoparticles to deliver. It then fits tightly into the O-ring fitting. The solenoid is wired to a trigger that consists of a momentary switch which fires a one-shot relay switch. The 120V AC current powers both the relay and the solenoid.

An advantage of administering a protein or peptide via a biodegradable nanoparticle capable of producing an immune response is the ability to cause the immunogen to be effectively presented to the animal or human over an extended period of time. As used herein, the term "tissue cells" means cells residing in a tissue whereas the term "tissue" means an aggregation of similarly specialized cells united in the performance of a particular function. Animal tissue cells can be bombarded in situ and the tissue is transformed in situ in the animal in which it is to be maintained. In general, the polynucleic acid sequence carried by the biodegradable nano-projectile of the present invention is a recombinant construct of a gene and a regulatory element. The construct may take any suitable form, such as plasmid, a genomic viral DNA sequence, such as a bovine papillomavirus vector (see E. Chen et al., 299 *Nature* 529, 1982), a retroviral RNA sequence, derivatives of the foregoing, and synthetic oligonucleotides. One aspect of the invention provides a biodegradable nanoparticle of the present invention as the nano-projectile used in nano-projectile bombardment in animals for administering a bioactive agent.

The regulatory sequence is positioned in the polynucleic acid sequence in operative association with the gene so as to be capable of inducing transcription of the gene. Regulatory sequences which may be used to provide transcriptional control of the gene in the polynucleic acid sequence are generally: promoters which are operable in the target tissue cells. Other regulatory elements which may optionally be incorporated into the polynucleic acid sequence include enhancers, termination sequences, and polyadenylation sites, as known in the art, as necessary to obtain the desired degree of expression of the gene in the cell into which it is inserted.

By ways of examples, genes that code for proteins or peptides which produce an endocrine response are genes that code for Factor VIII, genes that code for plasminogen activators such as Tissue Plasminogen Activator and urokinase, genes that code for growth hormones such as human or bovine growth hormone, genes that code for insulin, and genes that code for releasing factors such as Luteinizing Hormone Releasing Hormone. An endocrine response is a physiological response in the animal at a point sufficiently removed from the transformed tissue region to require that the protein or peptide travel through the circulatory or lymphatic system of the subject.

Skin in an animal is formed from an outer epidermis, an underlying dermis, and a hypodermis. The dermis and/or the hypodermis are the preferred tissue targets when the object of the transformation is to administer a protein or peptide to the animal in a manner which will evoke a physiological response thereto in the animal.

Some aspects of the invention relate to a method of administering a bioactive agent in an animal subject by in situ nano-projectile bombardment, comprising: (a) selecting a target skin tissue of the animal subject, wherein the target skin tissue is selected from the group consisting of epidermis tissue, dermis tissue, and hypodermis tissue; (b) providing nano-projectiles, wherein the bioactive agent is encapsulated in the nano-projectiles, each nano-projectile being in a nano-particle form; and (c) accelerating the nano-projectiles at the animal subject so that the nano-projectiles contact the animal's epidermis at a speed sufficient to penetrate the epidermis -and lodge in the target skin-tissue. In one embodiment, the speed in the accelerating step is generated by a pressure source for firing a nano-projectile bombardment gun at less than about 80 psi.

One aspect of the invention provides a method of administering a bioactive agent in an animal subject by in situ nano-projectile bombardment, wherein the nano-projectiles are biodegradable. In one embodiment, the nano-projectiles are made of biodegradable material selected from the group consisting of poly(L-lactic acid), polyglycolic acid, poly (D,L-lactide-co-glycolide), poly (ester amides), polycaprolactone, and co-polymers thereof.

One aspect of the invention provides a method of administering a bioactive agent in an animal subject by in situ nano-projectile bombardment, wherein the nano-projectile comprises a positively charged shell substrate and a negatively charged core substrate. In one embodiment, the shell substrate comprises a material selected from the group consisting of chitosan, low molecular weight chitosan, chitin, chitosan oligosaccharides, and chitosan derivatives thereof. In another embodiment, the low molecular weight chitosan is characterized with a solubility in water at a pH range of between about 5.0 to 6.5, preferably about 6.0 to 6.2.

One aspect of the invention provides a method of administering a bioactive agent in an animal subject by in situ nano-projectile bombardment, wherein the core substrate comprises a material selected from the group consisting of γ-PGA, α-PGA, PGA derivatives, heparin, heparin analogs, low molecular weight heparin, glycosaminoglycans, and alginate.

One aspect of the invention provides a method of administering a bioactive agent in an animal subject -by in situ nano-projectile bombardment, wherein the nano-projectile is about 50 μm to 500 μm in size, preferably about 100 μm to 300 μm in size, and most preferably about 150, μm to 250 μm in size.

One aspect of the invention provides a method of administering a bioactive agent in an animal subject by in situ nano-projectile bombardment, wherein the bioactive agent is a protein, a peptide, plasmid protein, or insulin. In one embodiment, the molecular formula of the insulin is selected from the group consisting of $C_{254}H_{377}N_{65}O_{75}S_6$, $C_{257}H_{383}N_{65}O_{77}S_6$, $C_{256}H_{381}N_{65}O_{79}S_6$, and $C_{267}H_{404}N_{72}O_{78}S_6$.

One aspect of the invention provides a method of administering a bioactive agent in an animal subject by in situ nano-projectile bombardment, wherein the bioactive agent is selected from a group consisting of chondroitin sulfate, hyaluronic acid, calcitonin, vancomycdin, and a growth factor. In one embodiment, the growth factor is selected from the group consisting of Vascular Endothelial Growth Factor (VEGF), basic Fibroblast Growth Factor (bFGF), Platelet Derived Growth Factor (PDGF), Platelet Derived Angiogenesis Factor (PDAF), Transforming Growth Factor-β (TGF-β), Transforming Growth Factor-α (TGF-α), Platelet Derived Epidermal Growth Factor (PDEGF), Platelet Derived Wound Healing Formula (PDWHF), epidermal growth factor, insulin-like growth factor, acidic Fibroblast Growth Factor (aFGF), and combinations thereof.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A method of administering a bioactive agent in an animal subject by in situ nano-projectile bombardment, comprising:

(a) selecting a target skin tissue of the animal subject;

(b) providing nano-projectiles, wherein the bioactive agent is encapsulated in the nano-projectiles, each nano-projectile being in a biodegradable nanoparticle form, wherein a pharmaceutical composition of said nano-projectiles comprises a second component of low molecular weight chitosan, a third component that is negatively charged and a first component of said bioactive agent, wherein said second component dominates on a surface of said nano-projectiles; and (c) accelerating the nano-projectiles at the animal subject so that the nano-projectiles contact the animal's epidermis at a speed sufficient to penetrate the epidermis and lodge in said target skin tissue.

2. The method according to claim 1, wherein said third component comprises γ-PGA.

3. The method according to claim 1, wherein the nano-projectile is about 50 μm to 500 μm in size.

4. The method according to claim 1, wherein the bioactive agent is a protein or a peptide.

5. The method according to claim 1, wherein the bioactive agent is plasmid protein.

6. The method according to claim 1, wherein the speed in the accelerating step is generated by a pressure source for firing a nano-projectile bombardment gun, a pressure from said pressure source being less than about 80 psi.

7. The method according to claim 1, wherein the bioactive agent is insulin.

8. The method according to claim 1, wherein the third component is heparin.

9. The method according to claim 1, wherein the bioactive agent comprises a growth factor.

10. The method according to claim 1, wherein the bioactive agent comprises hormone.

* * * * *